United States Patent [19]

Lesher et al.

[11] 4,312,875

[45] Jan. 26, 1982

[54] 5-(PYRIDINYL)-6-(LOWER-ALKYL)-2(1H)-PYRIDINONES, 1,2-DIHYDRO-2-OXO-5-(PYRIDINYL)-6-(LOWER-ALKYL)NICOTINIC ACIDS AND LOWER-ALKYL ESTERS THEREOF, AND CARDIOTONIC USE THEREOF

[75] Inventors: George Y. Lesher; Chester J. Opalka, Jr., both of Schodack; Donald F. Page, East Greenbush, all of N.Y.

[73] Assignee: Sterling Drug Inc., New York, N.Y.

[21] Appl. No.: 204,726

[22] Filed: Nov. 6, 1980

Related U.S. Application Data

[63] Continuation-in-part of Ser. No. 135,100, Mar. 28, 1980.

[51] Int. Cl.$^3$ .................. C07D 401/04; A61K 31/44; A61K 31/455
[52] U.S. Cl. .................................... 424/266; 424/263; 546/257
[58] Field of Search ................ 546/257; 424/263, 266

[56] References Cited

U.S. PATENT DOCUMENTS 4,004,012  1/1977  Lesher et al. .
4,072,746  2/1978  Lesher et al. .

*Primary Examiner*—John M. Ford
*Attorney, Agent, or Firm*—Robert K. Bair; B. Woodrow Wyatt

[57] ABSTRACT

1-$R_1$-6-(lower-alkyl)-5-(pyridinyl)-2(1H)-pyridinones or 1-$R_1$-1,2-dihydro-2-oxo-6-(lower-alkyl)-5-(pyridinyl)-nicotinic acids or lower-alkyl esters thereof or pharmaceutically-acceptable acid-addition or cationic salts thereof are useful as cardiotonic agents, where $R_1$ is hydrogen, lower-alkyl or lower-hydroxyalkyl. These compounds are prepared by hydrolyzing the corresponding 3-cyano compounds to produce the corresponding 3-carboxylic acids and then either by decarboxylating or esterifying the acids.

18 Claims, No Drawings

5-(PYRIDINYL)-6-(LOWER-ALKYL)-2(1H)-PYRIDI-NONES, 1,2-DIHYDRO-2-OXO-5-(PYRIDINYL)-6-(LOWER-ALKYL)NICOTINIC ACIDS AND LOWER-ALKYL ESTERS THEREOF, AND CARDIOTONIC USE THEREOF

CROSS-REFERENCE TO RELATED APPLICATION

This application is a continuation-in-part of copending Application Ser. No. 135,100, filed Mar. 28, 1980. The 5-(pyridinyl)-6-(lower-alkyl)-2(1H)-pyridinones which are disclosed and claimed herein as cardiotonics are disclosed as intermediates for the preparation of the corresponding 3-halo compounds in copending application Ser. No. 198,461, filed Oct. 20, 1980, a continuation-in-part of copending Application Ser. No. 97,504, filed Nov. 26, 1979 and now abandoned. Some of said 5-(pyridinyl)-6-(lower-alkyl)-2(1H)-pyridinones are also disclosed as intermediates for preparing 2-halo-5-(pyridinyl9-6-(lower-alkyl)pyridines in copending Applications Ser. Nos. 135,100, 135,105 and 135,211, all filed Mar. 28, 1980.

Some of the 1,2-dihydro-6-(lower-alkyl)-2-oxo-5-(pyridinyl)nicotinic acids, which are disclosed as cardiotonics and claimed herein, were disclosed as intermediates for preparing 6-(lower-alkyl)-3-nitro-5-(pyridinyl)-2(1H)-pyridinones in copending applications Ser. Nos. 135,100, 135,105 and 135,211, all filed Mar. 28, 1980.

BACKGROUND OF THE INVENTION (a) Field of the Invention

This invention relates to 6-(lower-alkyl)-5-(pyridinyl)-2(1H)-pyridinones, their use as cardiotonic agents, and their preparation.

(b) Description of the Prior Art

Lesher and Opalka (U.S. Pat. Nos. 4,004,012, issued Jan. 18, 1977; and 4,072,746, issued Feb. 7, 1978) show as cardiotonic agents 3-amino(or cyano)-5-(pyridinyl)-2(1H)-pyridinones and also 3-unsubstituted-5-(pyridinyl)-2(1H)-pyridinones, which were prepared by heating the corresponding 3-cyano compounds with aqueous sulfuric acid, first forming the 3-carboxylic acids, i.e., 1,2-dihydro-2-oxo-5-(pyridinyl)nicotinic acids, which are then decarboxylated. No cardiotonic activity is shown for said 1,2-dihydro-2-oxo-5-(pyridinyl)nicotinic acids. The disclosure of U.S. Pat. No. 4,072,746 also is shown in Lesher and Opalka U.S. Pat. Nos. 4,107,315, 4,137,233, 4,199,586 and 4,225,715.

SUMMARY OF THE INVENTION

In a composition of matter aspect, the invention relates to 1-$R_1$-5-PY-6(lower-alkyl)-2(1H)-pyridinones, which are useful as cardiotonic agents, where $R_1$ and PY are defined hereinbelow.

The invention in a process aspect relates to the process of producing 1-$R_1$-5-PY-6-(lower-alkyl)-2(1H)-pyridinones which comprises heating 1-$R_1$-1,2-dihydro-6-(loweralkyl)-2-oxo-5-PY-nicotinonitrile or 1-$R_1$-1,2-dihydro-6-(lower-alkyl)-2-oxo-5-PY-nicotinic acid with an aqueous mineral acid.

A composition aspect of the invention relates to a cardiotonic composition for increasing cardiac contractility in a patient, said composition comprising a pharmaceutically-acceptable carrier and, as the active ingredient thereof, a cardiotonically-effective amount of a 1-$R_1$-5-PY-6-(lower-alkyl)-2(1H)-pyridinone.

In a method aspect, the invention relates to a method for increasing cardiac contractility in a patient requiring such treatment which comprises the administration of a medicament comprising a pharmaceutically-acceptable carrier and, as the active component thereof, a cardiotonically-effective amount of a 1-$R_1$-5-PY-6-(lower-alkyl)-2(1H)-pyridinone.

In another composition of matter aspect, the invention relates to 1-$R_1$-1,2-dihydro-2-oxo-5PY-6-(lower-alkyl)nicotinic acids and lower-alkyl esters thereof, which are useful as cardiotonic agents.

Another process aspect of the invention relates to the process of hydrolyzing 1-$R_1$-1,2-dihydro-2-oxo-5-PY-6-(lower-alkyl)nicotinonitrile to produce the corresponding nicotinic acid.

Another composition aspect of the invention relates to a cardiotonic composition for increasing cardiac contractility in a patient, said composition comprising a pharmaceutically-acceptable carrier and, as the active ingredient thereof, a cardiotonically-effective amount of a 1-$R_1$-1,2-dihydro-2-oxo-5-PY-6-(lower-alkyl)nicotinic acid or lower-alkyl ester thereof.

In another method aspect, the invention relates to a method for increasing cardiac contractility in a patient requiring such treatment which comprises the administration of a medicament comprising a pharmaceutically-acceptable carrier and, as the active component thereof, a cardiotonically-effective amount of a cardiotonic 1-$R_1$-1,2-dihydro-2-oxo-5-PY-6-(lower-alkyl)nicotinic acid or lower-alkyl ester thereof.

DETAILED DESCRIPTION INCLUSIVE OF PREFERRED EMBODIMENTS

In a composition aspect the invention resides in the compounds having formula I

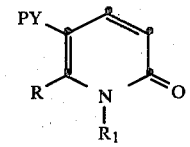

where $R_1$ is hydrogen, lower-alkyl or lower-hydroxyalkyl, R is lower-alkyl and PY is 4- or 3- or 2-pyridinyl or 4- or 3- or 2-pyridinyl having one or two lower-alkyl substituents, or pharmaceutically-acceptable acid-addition or cationic salt thereof. The compounds of formula I are useful as cardiotonic agents, as determined by standard pharmacological evaluation procedures. The compounds of formula I also are useful as intermediates for preparing the corresponding 3-halo compounds whose preparation is shown in said copending application Ser. No. 198,461, filed Oct. 20, 1980. Preferred embodiments are those of formula I where PY is 4-pyridinyl or 3-pyridinyl and R is methyl or ethyl. Particularly preferred embodiments are 6-methyl-5-(4-pyridinyl)-2(1H)-pyridinone ((I where $R_1$ is H, PY is 4-pyridinyl and R is methyl) and 6-ethyl-5-(4-pyridinyl)-2(1H)-pyridinone (I where $R_1$ is H, PY is 4-pyridinyl and R is ethyl), or pharmaceutically-acceptable acid-addition salt thereof. These particularly preferred embodiments were found to have significantly higher cardiotonic activity than the corresponding known 6-(desalkyl) compound, 5-(4-pyridinyl)-2(1H)pyridinone.

In a process aspect the invention resides in the process for producing 1-$R_1$-5-PY-6-R-2(1H)-pyridinone (I), which comprises heating 1-$R_1$-1,2-dihydro-2-oxo-5-PY-6-R-nicotinonitrile or 1-$R_1$-1,2-dihydro-2-oxo-5-PY-6-R-nicotinic acid with an aqueous mineral acid.

Another composition of matter aspect of the invention resides in the compounds having formula II

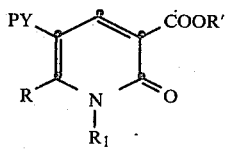

where $R_1$ R, and PY are defined as in formula I above and R' is hydrogen or lower-alkyl, or pharmaceutically-acceptable acid-addition or cationic salt thereof. The compounds of formula II are useful as cardiotonic agents, as determined by standard pharmacological evaluation procedures. Preferred embodiments are those of formula II where PY is 4-pyridinyl or 3-pyridinyl and R is methyl or ethyl.

In another process aspect the invention comprises hydrolyzing 1-$R_1$-1,2-dihydro-2-oxo-5-PY-6-R-nicotinonitrile to produce 1-$R_1$-1,2-dihydro-2-oxo-5-PY-6-(lower-alkyl)nicotonic acid and esterifying said nicotinic acid (II where R' is H) with a lower-alkanol to produce II where R' is lower-alkyl, where $R_1$, PY and R have the meanings given above for formula II.

A composition aspect of the invention resides in a cardiotonic composition for increasing cardiac contractility, said composition comprising a pharmaceutically-acceptable carrier and, as the active component thereof, a cardiotonically-effective amount of a 1-$R_1$-5-PY-6-R-2(1H)-pyridinone having formula I, where $R_1$, PY and R are each defined as in formula I or pharmaceutically-acceptable acid-addition or cationic salt thereof.

A method aspect of the invention resides in the method for increasing cardiac contractility in a patient requiring such treatment which comprises administering to such patient a cardiotonically-effective amount of a 1-$R_1$-5-PY-6-R-2(1H)-pyridinone having formula I, where $R_1$, PY and R are each defined as in formula I, or pharmaceutically-acceptable acid-addition or cationic salt thereof.

Another composition aspect of the invention resides in a cardiotonic composition for increasing cardiac contractility, said composition comprising a pharmaceutically-acceptable carrier and, as the active component thereof, a cardiotonically-effective amount of a 1-$R_1$-1,2-dihydro-2-oxo-5-PY-6-R-nicotinic acid or lower-alkyl ester thereof having formula II where $R_1$, PY and R are each defined as in formula II or pharmaceutically-acceptable acid-addition or cationic salt thereof.

Another method aspect of the invention resides in the method for increasing cardiac contractility in a patient requiring such treatment which comprises administering to such patient a cardiotonically-effective amount of a 1-$R_1$-1,2-dihydro-2-oxo-5-PY-6-R-nicotinic acid or lower-alkyl ester thereof having formula II where $R_1$, PY and R are each defined as in formula II or pharmaceutically-acceptable acid-addition or cationic salt thereof.

The term "lower-alkyl" as used herein, e.g., as the meaning of R, as one of the meanings of $R_1$, or R', or as a substituent for PY in formula I or II, means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-hydroxyalkyl", as used herein, e.g., as one of the meanings for $R_1$ in formula I or II, means hydroxyalkyl radicals having from two to six carbon atoms and having its hydroxy group and its free valence bond (or connecting linkage) on different carbon atoms, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxypentyl, 6-hydroxyhexyl, and the like.

Illustrative of PY in formula I or II where PY is 4-, 3-or 2-pyridinyl having 1 or 2 lower-alkyl substituents are the folllowing: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 4-methyl-2-pyridinyl, 6-methyl-2-pyridinyl, 2,3-dimethyl-4-pyridinyl, 2,6-dimethyl-4-pyridinyl, 4,6-dimethyl-2-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compounds of formulas I and II are useful both in the free base form and in the form of acid-addition salts, and, both forms are within the purview of the invention. The acid-addition salts are simply a more convenient form for use; and in practice, use of the salt form inherently amount to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound (I or II) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I or II) are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

Other pharmaceutically-acceptable salts of said compound of formula I or II are those cationic salts derived from strong inorganic or organic bases, e.g., sodium hydroxide, potassium hydroxide, trimethylammonium hydroxide, to produce the corresponding 1- or N-cationic salt, e.g., sodium, potassium, trimethylammonium salts, respectively, that is, the cationic ion being attached to the 1- or N-position of the 2(1H)-pyridinone ring. Also, the compound of formula II where R' is hydrogen can react with a second mole of said strong base to form an O-cationic salt of the 3-carboxylic acid group.

The molecular structures of the compounds of formulas I and II were assigned on the basis of evidence provided by infrared, nuclear magnetic resonance and mass spectra, and by the correspondence of calculated and found values for the elemental analysis.

The manner of making and using the instant invention will now be generally described so as to enable a person skilled in the art of pharmaceutical chemistry to make and use the same, as follows.

The preparation of the intermediate 1-$R_1$-1,2-dihydro-2-oxo-5-PY-6-R-nicotinonitriles are described in the next three paragraphs. These intermediate nicotinonitriles are disclosed and claimed as cardiotonics in copending application Ser. No. 97,504, filed Nov. 26, 1979, and in its copending continuation-in-part application Ser. No. 198,461, filed Oct. 20, 1980.

The preparation of 1-PY-2-(dimethylamino)ethenyl lower-alkyl ketone by reacting PY-methyl lower-alkyl ketone with dimethylformamide di-(lower-alkyl) acetal is carried out by mixing the reactants in the presence or absence of a suitable solvent. The reaction is conveniently run at room temperature, i.e., about 20°–25° C., or by warming the reactants up to about 100° C., preferably in an aprotic solvent, conveniently hexamethylphosphoramide because of the method used to prepare the PY-methyl lower-alkyl ketone, as noted below in Example A-1. Other suitable solvents include tetrahydrofuran, dimethylformamide, acetonitrile, ether, benzene, dioxane, and the like. Also, the reaction can be run without solvent, preferably using an excess of dimethylformamide di-(lower-alkyl)acetal. This procedure is further illustrated hereinbelow in Examples A-1 through A-17.

The intermediate PY-methyl lower-alkyl ketones are generally known compounds which are prepared by known methods, e.g., as given in Rec. trav. chim 72, 522 (1953); U.S. Pat. No. 3,133,077 (5-12-64); Bull. Soc. Chim 1968, 4132; Chem. Abstrs. 79, 8539h (1973); Chem. Abstrs. 81, 120,401a (1974); J. Org. Chem. 39, 3834 (1974); Chem. Abstrs. 87, 659q (1977); J. Org. Chem. 43, 2286 (1978).

The reaction of 1-PY-2-(dimethylamino)ethenyl lower-alkyl ketone with N-$R_1$-α-cyanoacetamide to produce 1-$R_1$-1,2-dihydro-2-oxo-5-PY-6-R-nicotinonitrile is carried out preferably by heating the reactants in a suitable solvent in the presence of a basic condensing agent. The reaction is conveniently run using an alkali lower-alkoxide, preferably sodium methoxide or ethoxide, in dimethylformamide. In practicing the invention, the reaction was carried out in refluxing dimethylformamide using sodium methoxide. Alternatively, methanol and sodium methoxide or ethanol and sodium ethoxide can be used as solvent and basic condensing agent, respectively; however, a longer heating period is required. Other basic condensing agents and solvents include sodium hydride, lithium diethylamide, lithium diisopropylamide, and the like, in an aprotic solvent, e.g., tetrahydrofuran, acetonitrile, ether, benzene, dioxane, and the like. This procedure is further illustrated hereinbelow in Examples B-1 through B-21.

The conversion of 1-$R_1$-1,2-dihydro-2-oxo-5-PY-6-R-nicotinonitrile to 1-$R_1$-5-PY-6-R-2(1H)-pyridinone (I, Q is hydrogen) is carried out by heating said nicotinonitrile with an aqueous mineral acid, preferably 50% sulfuric acid, first to form the corresponding nicotinic acid (II, R'=H) and then continue heating for a longer period whereupon the nicotinic acid is decarboxylated to produce I. This procedure is further illustrated hereinbelow in Examples C-1 through C-21.

The hydrolysis of 1-$R_1$-1,2-dihydro-2-oxo-5-PY-6-R-nicotinonitrile to produce 1-$R_1$-1,2-dihydro-2-oxo-5-PY-6-R-nicotonic acid (II, R' is H) is conveniently run by heating said nicotinonitrile on a steam bath with an aqueous mineral acid, preferably 50% sulfuric acid. This procedure is further illustrated hereinbelow in Examples D-1 through D-21.

The esterification of 1-$R_1$-1,2-dihydro-2-oxo-5-PY-6-R-nicotinic acid (II, R' is H) to produce lower-alkyl 1-$R_1$-1,2-dihydro-2-oxo-5-PY-6-R-nicotinate (II, R' is lower-alkyl) is carried by heating the acid (II, R' is H) with a lower-alkanol at about 25° C. to 150° C., preferably about 50° C. to 100° C. preferably in the presence of a suitable solvent, e.g., excess lower-alkanol, and in the presence of an acid catalyst, e.g., a strong inorganic acid or an organic sulfonic acid such as hydrochloric acid, sulfuric acid, methanesulfonic acid, p-toluenesulfonic acid, and the like. This procedure is further illustrated hereinbelow in Examples E-1 through E-19.

The following examples will further illustrate the invention without, however, limiting it thereto.

A. 1-PY-2-(DIMETHYLAMINO)ETHENYL LOWER ALKYL KETONES

A-1.—1-(4-Pyridinyl)-2-(dimethylamino)ethenyl methyl ketone—A mixture containing 20 g. of (4-pyridinyl)-methyl methyl ketone [alternatively named 1-(4-pyridinyl)-2-propanone] and 30 cc. of hexamethylphosphoramide was diluted with 65 cc. of dimethylformamide dimethyl acetal and the resulting mixture was refluxed for 30 minutes. TLC analysis showed a single spot, thereby indicating completion of the reaction (in another run, the reaction appeared to be complete after 30 minutes at room temperature). The reaction mixture was evaporated under reduced pressure using a rotary evaporator and a pressure of about 15 mm., thereby resulting in a crystalline residue weighing 24 g. The residue was purified by continuous chromatographic extraction on alumina (about 150 g.) using chloroform (recycled by distillation onto the alumina) as eluant. After 1 and ½ hours, the extract was heated in vacuo to remove the chloroform, thereby leaving, as a light yellow crystalline material, 23.2 g. of 1-(4-pyridinyl)-2-(dimethylamino)ethenyl methyl ketone, alternatively named 4-dimethylamino-2-(4-pyridinyl)-3-buten-2-one.

The above preparation can be carried out using in place of hexamethylphosphoramide other solvents, e.g., dimethylformamide, acetonitrile or others noted above or in the absence of a solvent; however, hexamethylphosphoramide was conveniently used since (4-pyridinyl)methyl methyl ketone was conveniently prepared as a mixture together with hexamethylphosphoramide, as seen by the following preparation: To a stirred solution containing 70 cc. of freshly distilled diisopropylamine and 200 cc. of tetrahydrofuran at 0° C. under nitrogen was added dropwise over 20 minutes 210 cc. of 2.4 M n-butyllithium in n-hexane and the reaction mixture was stirred for about 35 minutes at about 0°–5° C. To the cold solution was added dropwise over a period of 10 minutes 90 cc. of dry hexamethylphosphoramide (no temperature change) and a resulting light yellow solution was stirred for 15 minutes. To the cold solution at 0° C. was added a solution of 50 cc. of 4-picoline in 150 cc. of dry tetrahydrofuran over a 15 minute period and stirring was continued for 30 minutes at 0° C. Next, a mixture containing 50 cc. of dry ethyl acetate and 150 cc. of tetrahydrofuran was added over a 15 minute period (temperature rose from 0° to about 6° C.) and the resulting mixture was stirred for 20 minutes at 0° C. The ice bath was then removed and stirring continued for another 90 minutes whereupon the temperature of the reaction mixture rose to about 25° C. The reaction mixture was then cooled in an ice bath and to it was added 60 cc. of acetic acid over a period of about 30 minutes. The tetrahydrofuran was distilled off using a rotary evaporator in vacuo. The remaining mixture was diluted with 400 cc. of water and the aqueous mixture was extracted successively with two 250 cc. portions of isopropyl acetate and three 80 cc. portions of chloroform. The solvents were distilled off under reduced pressure to yield about 137 g. of a mixture consisting primarily of the desired product and hexamethylphosphoramide. Another run using the same quantities was carried out as above except after the addition of 60 cc. of glacial acetic acid, the mixture was diluted with only 200 cc. of water, the phases were separated, and the aqueous phase was extracted with five 100 ml. portions of chloroform. The chloroform extract was washed with saline solution and the chloroform was distilled off in vacuo. The remaining mixture of the desired ketone and hexamethylphosphoramide was combined with the above 137 g. of the same mixture and the combined mixture was distilled under reduced pressure to yield the following fractions: I. 63 g., b.p. of 110°–112° C. at 4 mm.; II. 59 g. of pale yellow oil, b.p. 113°–115° C. at 3 mm.; and, III. 69 g. of pale yellow oil, b.p. 115°–118° C. at 2.5 mm. Examination of fraction III by NMR showed it to consist of a 2:3 mixture by weight of (4-pyridinyl)methyl methyl ketone and hexamethylphosphoramide.

Acid-addition salts of 1-(4-pyridinyl)-2-(dimethylamino)ethenyl methyl ketone are conveniently prepared by adding to a mixture of 5 g. of 1-(4-pyridinyl)-2-(dimethylamino)ethenyl methyl ketone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1-(4-pyridinyl)-2-(dimethylamino)ethenyl methyl ketone and the appropriate acid, e.g., lactic acid or hydrochloric acid, to prepare respectively the monolactate or monohydrochloride salt in aqueous solution.

A-2.—1-(4-Pyridinyl)-2-(dimethylamino)ethenyl ethyl ketone—A mixture containing 87.5 g. of (4-pyridinyl)methyl ethyl ketone [alternatively named 1-(4-pyridinyl)-2-butanone] and 160 cc. of hexamethylphosphoramide was diluted with 100 g. of dimethylformamide dimethyl acetal and the resulting mixture was stirred under nitrogen at room temperature for 45 minutes. The methanol formed by the reaction was distilled off in vacuo using a rotary evaporator and the remaining material was distilled under reduced pressure to yield two fractions, one boiling at 45°–80° C. at 0.5 mm. and the second at 90°–95° C. at 0.5 mm. After TLC analysis showed predominantly a single spot for each fraction, the two fractions were combined (135 g.) and taken up in 600 cc. of chloroform. The resulting solution was washed with two 300 cc. portions of water and the water was back extracted with three 100 cc. portions of chloroform. The combined chloroform solution was dried over anhydrous sodium sulfate and purified by continuous extraction chromatography on 300 cc. of alumina using chloroform (recycled by distillation onto the alumina) as the eluant. The chloroform was distilled off in vacuo to yield a red oil which crystallized on standing overnight in an ice bath. The crystalline material was dissolved in carbon tetrachloride, cyclohexane was added and the mixture cooled to yield 64 g. of the resulting yellow crystalline product, 1-(4-pyridinyl)-2-(dimethylamino)ethenyl ethyl ketone. Another 11 g. of crystalline product was obtained from the mother liquor by continuous extraction chromatography on alumina using chloroform (recycled by distillation onto the alumina) as the eluant.

The above intermediate (4-pyridinyl)methyl ethyl ketone was obtained in a mixture with hexamethylphosphoramide as follows: To a mixture containing 200 cc. of tetrahydrofuran and 70 cc. of diisopropylamine under nitrogen at 0°–5° C. was added 210 cc. of 2.4 N n-butyllithium in n-hexane and the resulting mixture was stirred for 30 minutes. Next was added over a 10 minute period 90 cc. of hexamethylphosphoramide followed by stirring of the mixture for 15 minutes. Then was added over a 15 minute period a solution of 48 cc. of 4-picoline in 150 cc. of tetrahydrofuran followed by stirring for 30 minutes at about 0° C. The ice/acetone bath cooling the reaction mixture was replaced with a dry ice/acetone bath and to the reaction mixture was added over a 20 minute period a mixture of 75 cc. of ethyl propionate in an equal volume of tetrahydrofuran. The reaction mixture was then allowed to warm up to room temperature over a period of about 90 minutes and then was warmed at about 35° C. for 30 minutes. The mixture was next cooled in an ice/acetone bath and to it was added 60 cc. of glacial acetic acid over 30 minutes. The resulting pale yellow suspension was diluted with 200 cc. of water. The mixture was extracted with three 150 cc. portions of ethyl acetate and the ethyl acetate extract was back washed with saline solution. The extract was heated in vacuo to remove the ethyl acetate and the residue was taken up again with ethyl acetate. The solution was washed with water and then heated in vacuo to remove the ethyl acetate followed by heating the residue in vacuo at 50° C. for about 30 minutes to yield 100 g. of pale yellow oil. The pale yellow oil was combined with corresponding samples obtained from two additional runs and then distilled in vacuo to yield a 256 g. fraction, b.p. 85°–105° C. at 0.5–1.0 mm. The NMR of this fraction showed it to be a mixture of (4-pyridinyl)methyl ethyl ketone and hexamethylphosphoramide in a respective molar ratio of 1:1.55, that is, 35% or 0.35×256×90 g. of said ketone.

A-3. 1-(4-Pyridinyl)-2-(dimethylamino)ethenyl n-propyl ketone—A mixture containing 80 g. of (4-pyridinyl)methyl n-propyl ketone [alternatively named 1-(4-pyridinyl)-2-pentanone] and 46 cc. of hexamethylphosphoramide was diluted with 250 cc. of acetonitrile. To the mixture was added 90 cc. of dimethylformamide dimethyl acetal and the resulting reaction mixture was heated on a steam bath for ninety minutes and then distilled under vacuum at about 2 mm. to remove volatile materials, including methanol, acetonitrile and hexamethylphosphoramide. The remaining residue was diluted with ethyl acetate and washed with water. The combined water washings were extracted with five 150 cc. portions of ethyl acetate. The combined ethyl acetate solutions were washed with saline solution, dried over anhydrous sodium sulfate, filtered and evaporated to dryness. The residue crystallized while standing in a freezer. The crystalline product was slurried with cyclohexane, filtered and dried overnight at 30° C. to produce, as a yellow crystalline product, 97 g. of 1-(4-pyridinyl)-2-(dimethylamino)ethenyl n-propyl ketone, m.p. 48°–50° C.

The above intermediate (4-pyridinyl)methyl n-propyl ketone was otained in a mixture with hexamethylphosphoramide as follows: To a stirred solution of 70 cc. of diisopropylamine in 200 cc. of tetrahydrofuran under nitrogen at about 0° C. (use of ice bath) was added 210 cc. of 2.4 N n-butyllithium over twenty minutes and the resulting mixture was stirred for 30 minutes at about 0° C. to the mixture was added with stirring over ten minutes 90 cc. of hexamethylphosphoramide and the resulting mixture was stirred for another ten minutes. Next 45 cc. of 4-picoline in 140 cc. of tetrahydrofuran was added dropwise over fifteen to twenty minutes. The resulting dark orange-brown solution was stirred at 0° C. for thirty minutes and then treated dropwise over an eighteen minute period a solution consisting of 68 cc. of ethyl butyrate in 68 cc. of tetrahydrofuran, the temperature rising from −8° C. to +8° to 10° C. The reaction mixture was removed from the ice bath and allowed to warm up to room temperature for over seventy-five minutes. The reaction mixture was re-cooled and to it was added dropwise over fifteen minutes 60 cc. of glacial acetic acid. A pale yellow solid separated, resulting in a suspension. The suspension was diluted with water and extracted with two 200 cc. portions of ethyl acetate. The ethyl acetate extract was washed with three 100 cc. portions of saline solution, dried over anhydrous sodium sulfate and evaporated in vacuo to yield 107 g. of a mixture consisting primarily of (4-pyridinyl)methyl n-propyl ketone and hexamethylphosphoramide. The mixture obtained in this run was combined with corresponding mixtures obtained in two other runs and the combined mixtures were distilled under vacuum to produce, as the major fraction, b.p. 80°–90° C. at 0.2 mm., a mixture consisting of 80 g. of (4-pyridinyl)methyl n-propyl ketone and 46 g. of hexamethylphosphoramide.

Following the procedure described in Example A-2 but using a molar equivalent quantity of the appropriate PY-methyl lower-alkyl ketone in place of (4-pyridinyl)methyl ethyl ketone, it is contemplated that the corresponding 1-PY-2-(dimethylamino)ethenyl lower-alkyl ketones of Examples A-4 thru A-17 can be obtained.

A-4. 1-(3-Pyridinyl)-2-(dimethylamino)ethenyl methyl ketone using (3-pyridinyl)methyl methyl ketone.

A-5. 1-(2-Pyridinyl)-2-(dimethylamino)ethenyl methyl ketone using (2-pyridinyl)methyl methyl ketone.

A-6. 1-(4-Pyridinyl)-2-(dimethylamino)ethenyl isopropyl ketone using (4-pyridinyl)methyl isopropyl ketone.

A-7. 1-(4-Pyridinyl)-2-(dimethylamino)ethenyl n-butyl ketone using (4-pyridinyl)methyl n-butyl ketone.

A-8. 1-(4-Pyridinyl)-2-(dimethylamino)ethenyl isobutyl ketone using (4-pyridinyl)methyl isobutyl ketone.

A-9. 1-(4-Pyridinyl)-2-(dimethylamino)ethenyl tert.-butyl ketone using (4-pyridinyl)methyl tert.-butyl ketone.

A-10. 1-(4-Pyridinyl)-2-(dimethylamino)ethenyl n-pentyl ketone using (4-pyridinyl)methyl n-pentyl ketone.

A-11. 1-(2-Methyl-4-pyridinyl)-2-(dimethylamino)ethenyl ethyl ketone using (2-methyl-4-pyridinyl)methyl ethyl ketone.

A-12. 1-(5-Methyl-2-pyridinyl)-2-dimethylamino)ethenyl methyl ketone using (5-methyl-2-pyridinyl)methyl methyl ketone.

A-13. 1-(5-Ethyl-2-pyridinyl)-2-(dimethylamino)ethenyl ethyl ketone using (5-ethyl-2-pyridinyl)methyl ethyl ketone.

A-14. 1-(3-Pyridinyl)-2-(dimethylamino)ethenyl ethyl ketone using (3-pyridinyl)methyl ethyl ketone.

A-15. 1-(4,6-Dimethyl-2-pyridinyl)-2-(dimethylamino)ethenyl methyl ketone using (4,6-dimethyl-2-pyridinyl)methyl methyl ketone.

A-16. 1-(6-Methyl-2-pyridinyl)-2-(dimethylamino)ethenyl isopropyl ketone using (6-methyl-2-pyridinyl)methyl isopropyl ketone.

A-17. 1-(2-Pyridinyl)-2-(dimethylamino)ethenyl n-hexyl ketone using (2-pyridinyl)methyl n-hexyl ketone.

B.

1-$R_1$-1,2-DIHYDRO-6-(LOWER-ALKYL)-2-OXO-5-PY-NICOTINONITRILES

B-1.—1,2-Dihydro-6-methyl-2-oxo-5-(4-pyridinyl)-nicotinonitrile, alternatively named 1,6-dihydro-2-methyl-6-oxo-[3,4′-bipyridine]-5-carbonitrile—To a mixture containing 23 g. of 1-(4-pyridinyl)-2-(dimethylamino)ethenyl methyl ketone and 11 g. of α-cyanoacetamide dissolved in 400 cc. of dimethylformamide was added with stirring 14 g. of sodium methoxide and the resulting reaction mixture was heated in an oil bath under gentle reflux for one hour. TLC analysis showed no starting material in the reaction mixture which was then concentrated in vacuo on a rotary evaporator to a volume of about 80 cc. The concentrate was treated with about 160 cc. of acetonitrile and the resulting mixture was stirred on a rotary evaporator with warming until homogenuous and then cooled. The crystalline product was collected, rinsed successively with acetonitrile and ether, and dried overnight at 55° C. to yield 28 g. of tan crystalline product, namely, sodium salt of 1,2-dihydro-6-methyl-2-oxo-5-(4-pyridinyl)nicotinonitrile, the presence of cyano being confirmed by IR analysis. An 8 g. portion of said sodium salt was dissolved in 75 cc. of hot water, the aqueous solution treated with decolorizing charcoal filtered, the filtrate again treated with decolorizing charcoal and filtered, and the filtrate acidified with 6 N-hydrochloric acid by dropwise addition to a pH of 3. The acidic mixture was diluted with ethanol and cooled. The crystalline product was collected, dried, recrystallized from dimethylformamide-water and dried to produce 3.75 g.

of 1,2-dihydro-6-methyl-2-oxo-5-(4-pyridinyl)-nicotinonitrile, m.p. >300° C.

Acid-addition salts of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)nicotinonitrile and the appropriate acid, e.g., lactic acid or hydrochloric acid, to prepare respectively the monolactate or monohydrochloride salt in aqueous solution.

B-2.—6-Ethyl-1,2-dihydro-2-oxo-5-(4-pyridinyl)-nicotinonitrile, alternatively named 2-ethyl-1,6-dihydro-6-oxo-[3,4'-bipyridine]-5-carbonitrile, m.p. >300° C., 11.6 g., was prepared following the procedure described above in Example B-1 using 20 g. of 1-(4-pyridinyl)-2-(dimethylamino)ethenyl ethyl ketone, 8.4 g. of α-cyanoacetamide, 16.2 g. of sodium methoxide and 250 cc. of dimethylacetamide (as solvent in place of dimethylformamide).

B-3.—1,2-Dihydro-2-oxo-6-n-propyl-5-(4-pyridinyl)-nicotinonitrile, alternatively named 1,6-dihydro-6-oxo-2-n-propyl-[3,4'-bipyridine]-5-carbonitrile, m.p. 232°–234° C., 9.9 g., was prepared following the procedure described above in Example B-1 using 85 g. of 1-(4-pyridinyl)-2-(dimethylamino)ethenyl n-propyl ketone, 36.5 g. of α-cyanoacetamide, 50 g. of sodium methoxide and 800 cc. of dimethylacetamide.

B-4.—1,2-Dihydro-1,6-dimethyl-2-oxo-5-(4-pyridinyl)nicotinonitrile, alternatively named 1,6-dihydro-1,2-dimethyl-6-oxo-(3,4'-bipyridine)-5-carbonitrile, m.p. 245°–248° C., 32.3 g., was prepared following the procedure described above in Example B-1 using 42.5 g. of 1-(4-pyridinyl)-2-(dimethylamino)ethenyl methyl ketone, 23.5 g. of N-methyl-α-cyanoacetamide, 6.7 g. of sodium methoxide, 400 ml. of methanol and a refluxing period of two hours.

Following the procedure described in Example B-2 but using a molar equivalent quantity of the appropriate 1-PY-2-(dimethylamino)ethenyl lower-alkyl ketone (III) in place of 1-(4-pyridinyl)-2-(dimethylamino)ethenyl ethyl ketone and the appropriate N-R₁-α-cyanoacetamide, it is contemplated that the corresponding 1-R₁-1,2-dihydro-2-oxo-5-PY-6-R-nicotinonitriles of Examples B-5 thru B-21 can be obtained.

B-5. 1,2-Dihydro-6-methyl-2-oxo-5-(3-pyridinyl)-nicotinonitrile, using 1-(3-pyridinyl)-2-dimethylamino)ethenyl methyl ketone and α-cyanoacetamide.

B-6. 1,2-Dihydro-6-methyl-2-oxo-5-(2-pyridinyl)-nicotinonitrile, using 1-(2-pyridinyl)-2-(dimethylamino)ethenyl methyl ketone and α-cyanoacetamide.

B-7. 1,2-Dihydro-6-isopropyl-2-oxo-5-(4-pyridinyl)-nicotinonitrile, using 1-(4-pyridinyl)-2-(dimethylamino)ethenyl isopropyl ketone and α-cyanoacetamide.

B-8. 6-n-Butyl-1,2-dihydro-2-oxo-5-(4-pyridinyl)-nicotinonitrile, using 1-(4-pyridinyl)-2-dimethylamino)ethenyl n-butyl ketone and α-cyanoacetamide.

B-9. 1,2-Dihydro-6-isobutyl-2-oxo-5-(4-pyridinyl)-nicotinonitrile, using 1-(4-pyridinyl)-2-dimethylamino)ethenyl isobutyl ketone and α-cyanoacetamide.

B-10. 1,2-Dihydro-2-oxo-5-(4-pyridinyl)-6-tert.-butylnicotinonitrile, using 1-(4-pyridinyl)-2-(dimethylamino)ethenyl tert.-butyl ketone and α-cyanoacetamide.

B-11. 1,2-Dihydro-2-oxo-6-n-pentyl-5-(4-pyridinyl)-nicotinonitrile, using 1-(4-pyridinyl)-2-(dimethylamino)ethenyl n-pentyl ketone and α-cyanoacetamide.

B-12. 6-Ethyl-1,2-dihydro-5-(2-methyl-4-pyridinyl)-2-oxonicotinonitrile, using 1-(2-methyl-4-pyridinyl)-2-(dimethylamino)ethenyl ethyl ketone and α-cyanoacetamide.

B-13. 1,2-Dihydro-6-methyl-5-(5-methyl-2-pyridinyl)-2-oxonicotinonitrile, using 1-(5-methyl-2-pyridinyl)-2-(dimethylamino)ethenyl methyl ketone and α-cyanoacetamide.

B-14. 6-Ethyl-5-(5-ethyl-2-pyridinyl)-1,2-dihydro-2-oxonicotinonitrile, using 1-(5-ethyl-3-pyridinyl)-2-(dimethylamino)ethenyl ethyl ketone and α-cyanoacetamide.

B-15. 6-Ethyl-1,2-dihydro-2-oxo-5-(2-pyridinyl)-nicotinonitrile, using 1-(3-pyridinyl)-2-(dimethylamino)ethenyl ethyl ketone and α-cyanoacetamide.

B-16. 1,2-Dihydro-5-(4,6-dimethyl-2-pyridinyl)-6-methyl-2-oxonicotinonitrile, using 1-(4,6-dimethyl-2-pyridinyl)-2-(dimethylamino)ethenyl methyl ketone and α-cyanoacetamide.

B-17. 1,2-Dihydro-6-isopropyl-5-(6-methyl-2-pyridinyl)-2-oxo-nicotinonitrile, using 1-(6-methyl-2-pyridinyl)-2-(dimethylamino)ethenyl isopropyl ketone and α-cyanoacetamide.

B-18. 1,2-Dihydro-6-n-hexyl-2-oxo-5-(2-pyridinyl)-nicotinonitrile using 1-(2-pyridinyl)-2-(dimethylamino)ethenyl n-hexyl ketone and α-cyanoacetamide.

B-19. 6-Ethyl-1,2-dihydro-1-(2-hydroxyethyl)-2-oxo-5-(4-pyridinyl)nicotinonitrile, using 1-(4-pyridinyl)-2-(dimethylamino)ethenyl ethyl ketone and N-(2-hydroxyethyl)-α-cyanoacetamide.

B-20. 1-Ethyl-1,2-dihydro-6-methyl-2-oxo-5-(4-pyridinyl)nicotinonitrile, using 1-(4-pyridinyl)-2-dimethylamino)ethenyl methyl ketone and N-ethyl-α-cyanoacetamide.

B-21. 1,6-Diethyl-1,2-dihydro-2-oxo-5-(4-pyridinyl)-nicotinonitrile, using 1-(4-pyridinyl)-2-(dimethylamino)ethenyl ethyl ketone and N-ethyl-α-cyanoacetamide.

C.
1-R₁-6-(LOWER-ALKYL)-5-PY-2(1H)-PYRIDINONES

C-1. 6-Methyl-5-(4-pyridinyl)-2(1H)-pyridinone, alternatively named 2-methyl-[3,4'-bipyridin]-6(1H)-one—A mixture of 5.3 g. of 1,2-dihydro-6-methyl-2-oxo-5-(4-pyridinyl)nicotinonitrile and 30 cc. of 85% sulfuric acid was heated to about 195° C., gently refluxed for twenty-four hours, cooled and added to ice. The aqueous mixture was brought to a pH of 8 by addition of concentrated aqueous sodium hydroxide solution. The resulting precipitate (product plus Na₂SO₄) was treated with chloroform and the chloroform solution filtered. The filtrate was concentrated in vacuo to remove the chloroform and the resulting crystalline residue was recrystallized from methylene dichlorideether and dried at 75° C. for four hours to produce 4.1 g. of 6-methyl-5-(4-pyridinyl)-2(1H)-pyridinone, m.p. 287°–288° C.

Acid-addition salts of 6-methyl 5-(4-pyridinyl)-2(1H)-pyridinone are conveniently prepared by adding to a mixture of 5 g. of 6-methyl-5-(4-pyridinyl)-2(1H)-pyridinone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 6-methyl-5-(4-pyridinyl)-2(1H)-pyridinone and the appropriate acid, e.g., lactic acid or hydrochloric acid, to prepare respectively the monolactate or monohydrochloride salt in aqueous solution.

C-2. 6-Ethyl-5-(4-pyridinyl)-2(1H)-pyridinone, alternatively named 2-ethyl-[3,4'-bipyridin]-6(1H)-one—A mixture containing 9 g. of 6-ethyl-1,2-dihydro-2-oxo-5-(4-pyridinyl)nicotinonitrile and 50 ml. of concentrated sulfuric acid was heated with stirring at 200° C. for twenty-four hours, cooled to about 40° C. and quenched in 200 ml. of ice water. After the aqueous solution had been basified with concentrated ammonium hydroxide, the separated solid was collected, recrystallized from isopropyl alcohol (70 ml.), and dried at 60° C. in vacuo to yield 3 g. of 6-ethyl-5-(4-pyridinyl)-2(1H)-pyridinone, m.p. 226°–228° C. A second crop of 0.4 g., m.p. 225°–227° C., was obtained by concentrating the filtrate to about 20 ml.

C-3. 6-n-Propyl-5-(4-pyridinyl)-2(1H)-pyridinone, alternatively named 2-(n-propyl)-[3,4'-bipyridin]-6(1H)-one, m.p. 179°–180° C., 3.4 g., was obtained following the procedure described in Example C-2 but using 10 g. of 1,2-dihydro-6-n-propyl-2-oxo-5-(4-pyridinyl)nicotinonitrile, 42.5 cc. of 85% sulfuric acid, and recrystallization from methylene dichloride-ether.

Following the procedure described in Example C-2 but using in place of 6-ethyl-1,2-dihydro-2-oxo-5-(4-pyridinyl)nicotinonitrile a molar equivalent quantity of the corresponding 1-$R_1$-1,2-dihydro-2-oxo-5-PY-6-(lower-alkyl)-nicotinonitrile, it is contemplated that there can be obtained the 1-$R_1$-PY-6-(lower-alkyl)-2(1H)-pyridinones of Examples C-4 through C-21.

C-4. 6-Methyl-5-(3-pyridinyl)-2(1H)-pyridinone.
C-5. 6-Isopropyl-5-(4-pyridinyl)-2(1H)-pyridinone.
C-6. 6-n-Butyl-5-(4-pyridinyl)-2(1H)-pyridinone.
C-7. 6-Isobutyl-5-(4-pyridinyl)-2(1H)-pyridinone.
C-8. 5-(4-Pyridinyl)-6-tert.-butyl-2(1H)-pyridinone.
C-9. 6-n-Pentyl-5-(4-pyridinyl)-2(1H)-pyridinone.
C-10. 6-Ethyl-5-(2-methyl-4-pyridinyl)-2(1H)-pyridinone.
C-11. 6-Ethyl-5-(3-pyridinyl)-2(1H)-pyridinone.
C-12. 1,6-Dimethyl-5-(4-pyridinyl)-2(1H)-pyridinone.
C-13. 6-Ethyl-1-(2-hydroxyethyl)-5-(4-pyridinyl)-2(1H)-pyridinone.
C-14. 1-Ethyl-6-methyl-5-(4-pyridinyl)-2(1H)-pyridinone.
C-15. 1,6-Diethyl-5-(4-pyridinyl)-2(1H)-pyridinone.
C-16. 6-Methyl-5-(2-pyridinyl)-2(1H)-pyridinone.
C-17. 6-Methyl-5-(5-methyl-2-pyridinyl)-2(1H)-pyridinone.
C-18. 6-Ethyl-5-(5-ethyl-2-pyridinyl)-2(1H)-pyridinone.
C-19. 6-Methyl-5-(4,6-dimethyl-2-pyridinyl)-2(1H)-pyridinone.
C-20. 6-Isopropyl-5-(6-methyl-2-pyridinyl)-2(1H)-pyridinone.
C-21. 6-n-Hexyl-5-(2-pyridinyl)-2(1H)-pyridinone.

D.
1-$R_1$-1,2-DIHYDRO-6-(LOWER-ALKYL)-2-OXO-5-PY-NICOTINIC ACIDS

D-1. 1,2-Dihydro-6-methyl-2-oxo-5-(4-pyridinyl)-nicotinic Acid, alternatively named 1,6-dihydro-2-methyl-6-oxo[3,4'-bipyridine]-5-carboxylic acid—A 30 g. portion of 1,2-dihydro-6-methyl-2-oxo-5-(4-pyridinyl)nicotinonitrile was added with stirring to a hot solution containing 220 cc. of water and 145 cc. of concentrated sulfuric acid. The reaction mixture was refluxed for seven hours (about 122° C.) and then allowed to stand over the weekend at room temperature. It was then diluted with water, cooled in an ice bath and treated dropwise with stirring with ammonium hydroxide to neutral pH. The resulting crystalline precipitate was collected, rinsed successively with three 100 cc. portions of water and several times with acetone and then ether, and dried at 80° C. The crystalline material was slurried with 200 cc. of chloroform and 200 cc. of methanol for thirty minutes and the mixture concentrated in vacuo to a volume of 150 cc. The crystalline product was collected and dried at 95° C. over $P_2O_5$ to yield about 24 g. of product. A 10 g. sample of product was heated with 200 cc. of water at incipient boiling, the mixture cooled and the solid collected and dried at 80° C. to yield 9 g. of 1,2-dihydro-6-methyl-2-oxo-5-(4-pyridinyl)nicotinic acid, m.p. >260° C.

Following the procedure described in Example D-1 but using in place of 1,2-dihydro-6-methyl-2-oxo-5-(4-pyridinyl)nicotinonitrile a molar equivalent quantity of the corresponding 1-$R_1$-1,2-dihydro-2-oxo-5-PY-6-(lower-alkyl)nicotinonitrile, it is contemplated that there can be obtained the 1-$R_1$-1,2-dihydro-2-oxo-5-PY-6-(lower-alkyl)nicotinic acids of Examples D-2 through D-21.

D-2. 6-Ethyl-1,2-dihydro-2-oxo-5-(4-pyridinyl)-nicotinic acid.
D-3. 1,2-Dihydro-6-methyl-2-oxo-5-(3-pyridinyl)-nicotinic acid.
D-4. 1,2-Dihydro-2-oxo-6-n-propyl-5-(4-pyridinyl)-nicotinic acid.
D-5. 1,2-Dihydro-2-oxo-6-isopropyl-5-(4-pyridinyl)-nicotinic acid.
D-6. 6-n-Butyl-1,2-dihydro-2-oxo-5-(4-pyridinyl)-nicotinic acid.
D-7. 1,2-Dihydro-6-isobutyl-2-oxo-5-(4-pyridinyl)-nicotinic acid.
D-8. 1,2-Dihydro-2-oxo-5-(4-pyridinyl)-6-tert.-butyl-nicotinic acid.
D-9. 1,2-Dihydro-2-oxo-6-n-pentyl-5-(4-pyridinyl)-nicotinic acid.
D-10. 6-Ethyl-1,2-dihydro-5-(2-methyl-4-pyridinyl)-2-oxonicotinic acid.
D-11. 6-Ethyl-1,2-dihydro-2-oxo-5-(3-pyridinyl)-nicotinic acid.
D-12. 1,2-Dihydro-1,6-dimethyl-2-oxo-5-(4-pyridinyl)nicotinic acid.
D-13. 6-Ethyl-1,2-dihydro-1-(2-hydroxyethyl)-2-oxo-5-(4-pyridinyl)nicotinic acid.
D-14. 1-Ethyl-1,2-dihydro-6-methyl-2-oxo-5-(4-pyridinyl)nicotinic acid.

D-15. 1,6-Diethyl-1,2-dihydro-2-oxo-5-(4-pyridinyl)nicotinic acid.

D-16. 1,2-Dihydro-6-methyl-2-oxo-5-(2-pyridinyl)nicotinic acid.

D-17. 1,2-Dihydro-6-methyl-5-(5-methyl-2-pyridinyl)-2-oxonicotinic acid.

D-18. 6-Ethyl-5-(5-ethyl-2-pyridinyl)-1,2-dihydro-2-oxonicotinic acid.

D-19. 1,2-Dihydro-6-methyl-5-(4,6-dimethyl-2-pyridinyl)-2-oxonicotinic acid.

D-20. 1,2-Dihydro-6-isopropyl-5-(6-methyl-2-pyridinyl)-2-oxonicotinic acid.

D-21. 1,2-Dihydro-6-n-hexyl-2-oxo-5-(2-pyridinyl)nicotinic acid.

E. LOWER-ALKYL 1-R₁-6-(LOWER-ALKYL)-1,2-DIHYDRO-2-OXO-5-PY-NICOTINATES

E-1. Ethyl 1,2-dihydro-6-methyl-2-oxo-5-(4-pyridinyl)nicotinate—A 4 g. portion of 1,2-dihydro-6-methyl-2-oxo-5-(4-pyridinyl)nicotinic acid is heated in 200 cc. of refluxing ethanol with 1 g. of methanesulfonic acid for eighteen hours. The excess ethanol is distilled off in vacuo and the residue is recrystallized from dimethylformamide to produce ethyl 1,2-dihydro-6-methyl-2-oxo-5-(4-pyridinyl)nicotinate as its methanesulfonic acid salt. The salt is dissolved in warm water annd the solution made basic with excess aqueous potassium carbonate solution. The solid that separates is collected, dried, recrystallized from isopropanol alcohol and dried to produce ethyl 1,2-dihydro-6-methyl-2-oxo-5-(4-pyridinyl)nicotinate.

Acid-addition salts of ethyl 1,2-dihydro-6-methyl-2-oxo-5-(4-pyridinyl)nicotinate are conveniently prepared by adding to a mixture of 5 g. of ethyl 1,2-dihydro-6-methyl-2-oxo-5-(4-pyridinyl)nicotinate in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of ethyl 1,2-dihydro-6-methyl-2-oxo-5-(4-pyridinyl)nicotinate and the appropriate acid, e.g., lactic acid or hydrochloric acid, to prepare respectively the monolactate or monohydrochloride salt in aqueous solution.

Following the procedure described in Example E-1 but using in place of 1,2-dihydro-6-methyl-2-oxo-5-(4-pyridinyl)nicotinic acid and ethanol molar equivalent quantities of the appropriate 1-R₁-1,2-dihydro-2-oxo-5-PY-6-(lower-alkyl)nicotinic acid and lower-alkanol, it is contemplated that there can be obtained the lower-alkyl 1-R₁-1,2-dihydro-2-oxo-5-PY-6-(lower-alkyl)nicotinates of Examples E-2 through E-19.

E-2. Methyl 1,2-dihydro-6-methyl-2-oxo-5-(4-pyridinyl)nicotinate.

E-3. Ethyl 6-ethyl-1,2-dihydro-2-oxo-5-(4-pyridinyl)nicotinate.

E-4. n-Propyl 1,2-dihydro-6-methyl-2-oxo-5-(3-pyridinyl)nicotinate.

E-5. Ethyl 1,2-dihydro-2-oxo-6-n-propl-5-(4-pyridinyl)nicotinate.

E-6. Isopropyl 1,2-dihydro-2-oxo-6-isopropyl-5-(4-pyridinyl)nicotinate.

E-7. Ethyl 6-n-butyl-1,2-dihydro-2-oxo-5-(4-pyridinyl)nicotinate.

E-8. Ethyl 1,2-dihydro-6-isobutyl-2-oxo-5-(4-pyridinyl)nicotinate.

E-9. Methyl 1,2-dihydro-2-oxo-5-(4-pyridinyl)-6-tert.-butylnicotinate.

E-10. Methyl 1,2-dihydro-2-oxo-6-n-pentyl-5-(4-pyridinyl)nicotinate.

E-11. n-Butyl 6-ethyl-1,2-dihydro-5-(2-methyl-4-pyridinyl)-2-oxonicotinate.

E-12. Ethyl 6-ethyl-1,2-dihydro-2-oxo-5-(3-pyridinyl)nicotinate.

E-13. Ethyl 1,2-dihydro-1,6-dimethyl-2-oxo-5-(4-pyridinyl)nicotinate.

E-14. Ethyl 6-ethyl-1,2-dihydro-1-(2-hydroxyethyl)-2-oxo-5-(4-pyridinyl)nicotinate.

E-15. Ethyl 1,6-diethyl-1,2-dihydro-2-oxo-5-(4-pyridinyl)nicotinate.

E-16. n-Hexyl 1,2-dihydro-6-methyl-2-oxo-5-(2-pyridinyl)nicotinate.

E-17. Methyl 6-ethyl-5-(5-ethyl-2-pyridinyl)-1,2-dihydro-2-oxonicotinate.

E-18. Ethyl 1,2-dihydro-6-methyl-5-(4,6-dimethyl-2-pyridinyl)-2-oxonicotinate.

E-19. Ethyl 1,2-dihydro-6-n-hexyl-2-oxo-5-(2-pyridinyl)nicotinate.

The usefulness of the compounds of formula I or II or salt thereof as cardiotonic agents is demonstrated by their effectiveness in standard pharmacological test procedures, for example, in causing a significant increase in contractile force in the Isolated Cat Atria and Papillary Muscle Procedure and in causing a significant increase in cardiac contractile force in the Anesthetized Dog Procedure with low or minimal changes in heart rate and blood pressure. Detailed descriptions of these test procedures appear in U.S. Pat. No. 4,072,746, issued Feb. 7, 1980.

When tested by the above-noted Isolated Cat Atria and Papillary Muscle Procedure, the compounds of formula I and II when tested at doses of 3, 10 or 30 μg./ml., were found to cause a significant increase, that is, greater than 25%, in papillary muscle force and a significant increase, that is, greater than 25%, in right atrial force, while causing only a low percentage increase (about one-third or less than the percentage increase in right atrial force or papillary muscle force) in right atrial rate. Moreover, the 6-(lower-alkyl) compounds of formula I unexpectedly were found to be markedly more active as cardiotonics when tested by this procedure in comparison with the corresponding prior art 6-des-(lower-alkyl) compounds. Also, the compounds of formula II where R' is hydrogen were found to be active as cardiotonics whereas, in contrast, the corresponding prior art 6-des-(lower-alkyl) compounds are shown only as intermediates, not as having cardiotonic properties.

The markedly higher cardiotonic activity of the 6-(lower-alkyl) compounds of formula I over the corresponding prior art 6-unsubstituted compounds is illustrated by the following comparisons of test data obtained using said isolated cat atria and papillary muscle procedure: the percentage increases in papillary muscle force and right atrial force for 6-methyl-5-(4-pyridinyl)-2(1H)-pyridinone were found to be 115% and 48% when tested at 10 μg/ml. compared with corresponding respective increases of 48% and 51% for prior art 5-(4-pyridinyl)-2(1H)-pyridinone tested at 100 μg./ml., that is, ten times the dose; the percentage increases in papillary muscle force and right atrial force for 6-ethyl-5-(4-pyridinyl)-2(1H)-pyridine were found to be 106% and 50% when tested at 30 µg./ml. compared with corresponding increases of 48% and 51% for 5-(4-pyridinyl)-2(1H)-pyridinone tested at 100 µg./ml., that is, more than three times the dose.

As illustrative of a cardiotonically-active compound of formula II where R' is hydrogen whereas the corresponding prior art 6-des-(lower-alkyl) compounds are shown only as intermediates and not as cardiotonic agents, 1,2-dihydro-6-methyl-2-oxo-5-(4-pyridinyl)nicotinic acid when tested by the similar in vitro guinea pig atria and papillary muscle test (comparison with corresponding in vitro cat atria and papillary muscle test given in the immediately following paragraphs) was found to show percentage increases in papillary muscle force and right atrial force of 36% and 27% at 30 µg./ml. respectively and 44% and 69% respectively at 100 µg./ml.

Cat or guinea pig atria papillary muscle test—Cats of either sex weighing 0.6 to 2.7 kg. were anesthetized with sodium pentobarbital, 30 mg./mg. i.v. and exsanguinated. Hartley guinea pigs of either sex weighing 650 to 800 g. were stunned with a sharp blow to the head and exsanguinated. Both cats and guinea pigs and their tissues were handled by the following procedures. The chest was opened rapidly, the heart excised, rinsed in Tyrode's solution, and the right atrium and one or more small thin right ventricular papillary muscles were excised. The tissues were transferred to a large Petri dish filled with modified Tyrode's solution oxygenated with 95% $O_2$, 5% $CO_2$. A silver wire was attached to each of two opposite ends of the papillary muscle or the atrial preparation. The wire from the nontendonous end of the papillary muscle was attached to a glass covered platinum electrode which was connected to the cathode of a Grass Model SD5 stimulator. The pouch end of the atrium was attached to the curved end of a glass rod. The preparations were mounted in organ baths (40 ml. for papillary muscles and 50 ml. for atrial) filled with modified Tyrode's solution maintained at 37° C. and oxygenated with 95% $O_2$, 5% $CO_2$. The wire on the tendonous end of the papillary muscle was looped and tied to a force-displacement transducer (Grass, FTO3C) and then connected to the anodal terminal of the stimulator. The second wire on the right atrium was tied to a forcedisplacement transducer and the atrium allowed to beat spontaneously. The transducer is connected to a Grass model 7 polygraph. The resting tension on each muscle was adjusted to produce a maximum contractile force (Starlings Law) and the muscle stimulated electrically at a rate of 120 beats/min. by a suprathreshold (1.5×threshold) rectangular pulse, 0.5 msec in duration.

After Starlings and voltage adjustment, the preparations were washed and allowed to equilibrate for 15 minutes before a test done of dopamine (1.0 µg./ml.) or isoproterenol (0.0003 µg./ml.) was added and the response monitored. Next, the test drug dissolved in vehicle or the vehicle alone was added to the tissue baths and the responses recorded. The tissues were washed at least two times after each dose or until the pre-drug control level in developed tension and rate was obtained. Five or six doses of drug were given to the preparations over a period of 4–5 hours.

The modified Tyrode's solution bathing the preparation had the following composition (in mM): NaCl, 136.9, KCl, 5.4; $NaH_2PO_4$, 0.4; $CaCl_2$, 1.8; $MgCl_2.6H_2O$, 1.0; $NaCHO_3$, 11.9 glucose, 5.5; EDTA, 0.04. The solution was equilibrated with a gas mixture consisting of 95% $O_2$ and 5% $CO_2$, and the pH was 7.3–7.4 at 37° C.

Tissue Differences—A comparison of cat and guinea pig tissue characteristics is presented as follows: The cat papillary muscles used averaged 5.12±0.20 mm in length and weighed 7.01±0.64 mg. with a mean cross sectional area of 1.31 mm² (N+26, N being the number of preparations). Guinea pig papillary muscles averaged 6.60±0.18 mm in length and weighed 9.09±0.47 mg. Their mean cross sectional area was 1.31 mm² (N=60). The resting tension (tension applied to the muscle to obtain maximum contractile force, Starling's Law) applied to cat papillary muscles averaged 1.5±0.09 g. (N=34) while the resting tension applied to guinea pig papillary muscles was 1.01±0.042 g. (N=56). Cat papillary muscle control active tension at the start of the day averaged 0.62±0.05 g. (N=34); the guinea pig papillary muscles averaged 0.213±0.011 g. (N=62). A comparison of cat and guinea pig papillary muscle active tension per mg. of tissue $$\left( \frac{\text{control active tension in mg}}{\text{wet weight of tissue in mg}} \right)$$

indicated that for their weight cat papillary muscles are almost 4 times stronger than guinea pig papillary muscles. The cat right atria weighed more than guinea pig right atria; 306±15 mg. (N=24) and 76.5±mg. (N−41) respectively. The average right atrial rate for cat atria was 133±3 beats/min. (n=34) while the rate for guinea pig atria was 167±3 beats/min. (n=57). The applied resting tension on guinea pig atria averaged 1.95±0.06 g. (N=117); on cat right atria the resting tension averaged 2.21±0.10 g. (N=34). A comparison of guinea pig and cat right atrial control active tension indicates that, similar to the papillary muscles form the two species, the cat muscle was stronger; 1.93±0.10 g. (N=34) active tension for cat atria and 0.742±0.04 g. (N=34) active tension for guinea pig atria. Because of the lower control active tensions of guinea pig tissues the percent change from control values for both rate and force responses is elevated. Thus, whereas cardiotonic activity is ascertained with a papillary muscle force or right atrial force increase of 26% and greater in the cat test, corresponding activity in the guinea pig test is designated with a papillary muscle force or right atrial force increase of 31% and greater.

When tested by the above-noted Anesthetized Dog Procedure, compounds of formula I were administered intravenously as a single bolus injection of 0.01, 0.03, 0.10 mg./kg. and higher caused a significant increase, that is, greater than 25%, in cardiac contractile force or cardiac contractility with only low or minimal changes (less than 25%) in heart rate and blood pressure. Moreover, the 6-(lower-alkyl) compounds of formula I were found to be markedly more active as cardiotonics when tested by this procedure in comparison with the corresponding prior art 6-des-(lower-alkyl) compounds, as evidenced by the following illustration: the percentage increase on the cardiac contractile forces or cardiac contractilities for 6-methyl-5-(4-pyridinyl)-2(1H)-pyridinone when tested as indicated in the anesthetized dog at 0.01, 0.03 and 0.10 mg./kg. intravenously were found to be 28.8%, 53.5% and 124.6% respectively compared with 41%, 70% and 92% for the corresponding prior art 6-desmethyl compound, that is, 5-(4- pyridinyl)-2(1H)-pyridinone, when tested at one hundred times the doses, that is, at 1, 3 and 10 mg./kg. intravenously, respectively.

The present invention includes within its scope a cardiotonic composition for increasing cardiac contractility, said composition comprising a pharmaceutically-acceptable carrier and, as the active component thereof, a cardiotonically-effective amount of a 1-$R_1$-6-(lower-alkyl)-5-PY-2(1H)-pyridinone of formula I or a 1-$R_1$-1,4-dihydro-2-oxo-6-(lower-alkyl)-5-PY-nicotinic acid or lower-alkyl ester thereof of fromula II or pharmaceutically-acceptable acid-addition or cationic salt thereof. The invention also includes within its scope the method for increasing cardiac contractility in a patient requiring such treatment which comprises administering to such patient a cardiotonically-effective amount of said 1-$R_1$-6-(lower-alkyl)-5-PY-2(1H)-pyridinone of formula I or 1-$R_1$-1,4-dihydro-2-oxo-6-(lower-alkyl)-5-PY-nicotinic acid or lower-alkyl ester thereof of formula II or pharmaceutically-acceptable acid-addition or cationic salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g, lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavouring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emusifying and dispersing agents.

They may be sterilized, for example by filtration through a bacteria-retaining filter, by incorporation of sterilising agents in the compositions, by irradiation or by heating. They may also be manufactured in the form of sterile solid composition which can be dissolved in sterile wate or some other sterile injectable medium immediately before use.

The percentages of active components in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 1-$R_1$-5-PY-6-R-2(1H)-pyridinone having the formula

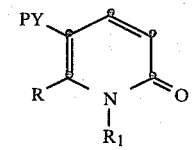

where $R_1$ is hydrogen, R is methyl or ethyl and PY if 4-, 3- or 2-pyridinyl or 4-, 3- or 2-pyridinyl having one or two lower-alkyl substitutents, or pharmaceutically-acceptable acid-addition or cationic salt thereof.

2. A compound according to claim 1 where PY is 4-pyridinyl.

3. 6-Methyl-5-(4-pyridinyl)-2(1H)-pyridinone or pharmaceutically-acceptable acid-addition salt thereof.

4. 6-Ethyl-5-(4-pyridinyl)-2(1H)-pyridinone or pharmaceutically-acceptable acid-addition salt thereof.

5. A 1-$R_1$-1,2-dihydro-5-PY-2-oxo-6-R-nicotonic acid or lower-alkyl ester thereof having the formula

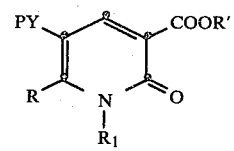

where $R_1$ is hydrogen, R is methyl or ethyl, R' is hydrogen or lower-alkyl and PY is 4-, 3- or 2-pyridinyl or 4-, 3- or 2-pyridinyl having one or two lower-alkyl substituents, or pharmaceutically-acceptable acid-addition or cationic salt thereof.

6. A compound according to claim 5 where R' is hydrogen.

7. A compound according to claim 5 where R' is lower-alkyl.

8. A compound according to claim 5 wherein PY is 4-pyridinyl or 3-pyridinyl.

9. 1,2-Dihydro-6-methyl-2-oxo-5-(4-pyridinyl)nicotinic acid or pharmaceutically-acceptable acid-addition salt thereof.

10. A cardiotonic composition for increasing cardiac contractility, said composition comprising a pharmaceutically-acceptable inert carrier and, as the active component thereof, a cardiotonically-effective amount of a 1-$R_1$-5-PY-6-R-2(1H)-pyridinone having the formula

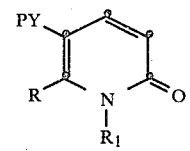

where $R_1$ is hydrogen, R is methyl or ethyl and PY is 4-, 3- or 2-pyridinyl or 4-, 3- or 2-pyridinyl having one or two lower-alkyl substituents, or pharmaceutically-acceptable acid-addition or cationic salt thereof.

11. A composition according to claim 10 where the active component is 6-methyl-5-(4-pyridinyl)-2(1H)-pyridinone or pharmaceutically-acceptable acid-addition salt thereof.

12. A composition according to claim 10 where the active component is 6-ethyl-5-(4-pyridinyl)-2(1H)-pyridinone or pharmaceutically-acceptable acid-addition salt thereof.

13. The method for increasing cardiac contractility in a patient requiring such treatment which comprises administering orally or parenterally in a solid or liquid dosage form to such a patient a cardiotonically-effective amount of a 1-R₁-5-PY-6-R-2(1H)-pyridinone having the formula

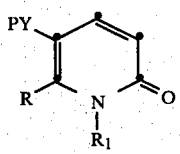

where R₁ is hydrogen, R is methyl or ethyl and PY is 4-, 3- or 2-pyridinyl or 4-, 3- or 2-pyridinyl having one or two lower-alkyl substitutents, or pharmaceutically-acceptable acid-addition or cationic salt thereof.

14. The method according to claim 13 where PY is 4-pyridinyl or 3-pyridinyl.

15. A cardiotonic composition for increasing cardiac contractility, said composition comprising a pharmaceutically-acceptable inert carrier and, as the active component thereof, a cardiotonically-effective amount of a 1-R₁-1,2-dihydro-2-oxo-5-PY-6-R-nicotinic acid or lower-alkyl ester thereof having the formula

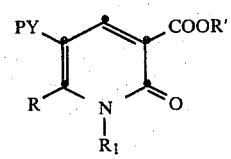

where R₁ is hydrogen, R is methyl or ethyl, R' is hydrogen or lower-alkyl and PY is 4-, 3- or 2-pyridinyl or 4-, 3- or 2-pyridinyl having one or two lower-alkyl substituents, or pharmaceutically-acceptable acid-addition or cationic salt thereof.

16. A composition according to claim 15 where the active component is 1,2-dihydro-6-methyl-2-oxo-5-(4-pyridinyl)nicotinic acid or pharmaceutically-acceptable acid-addition salt thereof.

17. The method for increasing cardiac contractility in a patient requiring such treatment which comprises administering orally or parenterally in a solid or liquid dosage form to such patient a cardiotonically-effective amount of a 1-R₁-1,2-dihydro-2-oxo-5-PY-6-R-nicotinic acid or lower-alkyl ester thereof having the formula

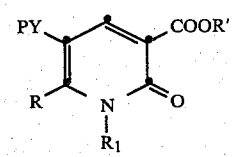

where R₁ is hydrogen, R is methyl or ethyl, R' is hydrogen or lower-alkyl and PY is 4-, 3- or 2-pyridinyl or 4-, 3- or 2-pyridinyl having one or two lower-alkyl substituents, or pharmaceutically-acceptable acid-addition or cationic salt thereof.

18. The method according to claim 17 where PY is 4-pyridinyl or 3-pyridinyl.

* * * * *

UNITED STATES PATENT AND TRADEMARK OFFICE
CERTIFICATE OF CORRECTION

PATENT NO. : 4,312,875
DATED : January 26, 1982
INVENTOR(S) : George Y. Lesher et al.

It is certified that error appears in the above-identified patent and that said Letters Patent are hereby corrected as shown below:

Column 1, line 22, "9" should read -- ) --.

Column 2, line 11, "5PY-6" should read -- 5-PY-6 --.

Column 4, line 34, "amount" should read -- amounts --.

Column 5, line 57, "659q" should read -- 6594q --.

Column 18, line 7, "(N+26," should read -- (N=26, --.

Column 18, line 29, "(N-41)" should read -- (N=41) --.

Column 19, line 11, "fromula" should read -- formula --.

Column 19, line 57, "composition" should read -- compositions --.

Column 19, line 58, "wate" should read -- water --.

Claim 1, line 4, "if" should read -- is --.

Signed and Sealed this

Twentieth Day of December 1983

[SEAL]

Attest:

GERALD J. MOSSINGHOFF

*Attesting Officer*  *Commissioner of Patents and Trademarks*